United States Patent
Adkins, Jr. et al.

(10) Patent No.: US 11,090,236 B2
(45) Date of Patent: Aug. 17, 2021

(54) HYPOCHLOROUS ACID-BASED EYELID CLEANSERS

(71) Applicant: OCuSOFT, Inc., Rosenberg, TX (US)

(72) Inventors: Nat Adkins, Jr., Richmond, TX (US);
Cynthia Barratt, Richmond, TX (US);
Thomas Mason, Cypress, TX (US);
Paramita Sarkar, Richmond, TX (US)

(73) Assignee: OCUSOFT, INC., Rosenberg, TX (US)

( * ) Notice: Subject to any disclaimer, the term of this patent is extended or adjusted under 35 U.S.C. 154(b) by 0 days.

(21) Appl. No.: 16/400,667

(22) Filed: May 1, 2019

(65) Prior Publication Data

US 2019/0336415 A1    Nov. 7, 2019

Related U.S. Application Data

(60) Provisional application No. 62/665,930, filed on May 2, 2018.

(51) Int. Cl.
| | | |
|---|---|---|
| *A61K 8/20* | (2006.01) | |
| *A61K 8/365* | (2006.01) | |
| *A61K 8/86* | (2006.01) | |
| *A61K 8/02* | (2006.01) | |
| *A61Q 17/00* | (2006.01) | |
| *A61Q 19/10* | (2006.01) | |

(52) U.S. Cl.
CPC ............. *A61K 8/20* (2013.01); *A61K 8/0208* (2013.01); *A61K 8/365* (2013.01); *A61K 8/86* (2013.01); *A61Q 17/005* (2013.01); *A61Q 19/10* (2013.01); *A61K 2800/522* (2013.01); *A61K 2800/5922* (2013.01); *A61K 2800/87* (2013.01)

(58) Field of Classification Search
CPC ........... A61K 8/20; A61K 8/86; A61Q 17/005
See application file for complete search history.

(56) References Cited

U.S. PATENT DOCUMENTS

| | | | |
|---|---|---|---|
| 6,309,663 B1* | 10/2001 | Patel ..................... | A61P 25/16 424/450 |
| 2005/0214386 A1 | 9/2005 | Shaheen et al. | |
| 2008/0131470 A1* | 6/2008 | Witham ................ | A61K 8/345 424/402 |
| 2010/0285151 A1* | 11/2010 | Goldan ................... | A61P 31/00 424/662 |
| 2013/0316001 A1 | 11/2013 | Popov et al. | |
| 2017/0202757 A1 | 7/2017 | Hoover | |
| 2018/0071192 A1 | 3/2018 | Adkins, Jr. et al. | |

FOREIGN PATENT DOCUMENTS

TW    201735910 A    10/2017

OTHER PUBLICATIONS

Miaskowska et al. "Statistical analysis of optimal ultrasound emulsification parameters in thistle-oil nanoemulsions", J Surfact Deterg, 2017, 20:233-246. (Year: 2017).*
Wikipedia, "Hydrophilic-lipophilic balance", May 9, 2016 (May 9, 2016), retrieved on Jul. 1, 2019 from https://en.wikipedia.org/w/index.php?title=Hydrophilic-lipophilic_balance&oldid=719445478; entire document, especially p. 1 para 1.

* cited by examiner

*Primary Examiner* — Gina C Justice
(74) *Attorney, Agent, or Firm* — D'Ambrosio & Menon, PLLC; Usha Menon

(57) ABSTRACT

An antimicrobial eyelid cleanser composition contains: (a) a hypohalous acid; (b) one or more surfactants having a HLB value of 5 to 18; and (c) an aqueous vehicle, the aqueous vehicle comprising: (i) one or more tonicity adjusters; (ii) one or more osmolality adjusters for adjusting an osmolality of the composition; and (iii) one or more pH adjusters for maintaining the pH of the composition at between about 4.5 to about 8.0. The composition can be dispensed in a foam, liquid, spray, mist, gel or lotion form. The composition can facilitate long term eyelid hygiene by removing excess oil, debris and desquamated skin and provide relief for inflammation of the eyes.

19 Claims, No Drawings

HYPOCHLOROUS ACID-BASED EYELID CLEANSERS

CROSS-REFERENCE TO RELATED APPLICATIONS

This application claims the benefit of Provisional U.S. Patent Application No. 62/665,930 filed May 2, 2018, and entitled "Hypochlorous Acid-Based Eyelid Cleansers," the entire content and disclosure of which, both express and implied, is incorporated herein by reference.

FIELD OF THE INVENTION

The present invention relates generally to eyelid and skin cleaning compositions and to methods of preparing and using such compositions.

BACKGROUND

Ocular health refers to eyes as well as structures associated with the eyes, eyelids for example. The eyelids are important in over-all ocular health because they protect the eyes from dangers such as approaching objects or from airborne contaminants, such as pollen, dust particles or other foreign bodies. The eyelids contain essential glands; the lacrimal glands and meibomian glands that produce layers of tear film that are critical for healthy eyes. When an individual blinks, a new tear film is created and tears are distributed across the cornea to lubricate the surface of the eye. This blinking action also "flushes" foreign materials from the eye.

The eyelids, however, are subject to certain problems, which while very common, are none-the-less bothersome, especially for contact lens wearers, and may lead to other more serious complications. One complication is blepharitis. Blepharitis is a common chronic inflammation of the eyelids characterized by a scaly crust on the lid margins. The condition may be caused by a bacterial infection, or it may be allergic in origin or associated with seborrhea of the face and scalp. Treatment usually involves cleansing the eyelids on a regular basis to remove excess oil, debris, and desquamated skin that may be problematic.

Often associated with or secondary to blepharitis is a bacterial infection of the surface of the skin at the edge of the lid known as an internal hordeolum. Other such infections include external hordeolum, commonly referred to as styes, which are infections of the tiny oil secreting meibomian glands along the edge of the eyelid, surrounding the eyelashes. A stye begins as a red, tender bump and usually fully develops within three days. Such conditions are accompanied by pain, redness and tenderness of the eyelid (or lid) margins. Although styes are often recurring, regular cleansing of the eyelid margins can minimize such conditions. A second problem is a chalazion, which is an inflammation of the meibomian glands inside the eyelid. Chalazia typically grow slowly over 2-3 weeks and although they do not typically cause pain, they often require surgical intervention if left untreated.

With any of the above-described problems, as well as other medical complications, such as rosacea and seborrhea, proper eyelid hygiene with the use of an eyelid cleanser may minimize the severity of the outbreak, or prevent the problem altogether if caught early. Eyelid cleansers are also used for cleaning eyelashes, eyelids or the periocular area and may be used as a pre-operative scrub to help reduce the presence of harmful bacteria which may cause infection, inflammation, or even endophthalmitis in patients.

SUMMARY

Compositions containing hypochlorous acid and water have been used successfully along with other eyelid care compositions to facilitate long term eyelid hygiene, as has been described in Applicant's U.S. Pat. No. 9,833,399. However, Applicant has determined that there is a need for a single isotonic/isoosmolar and physiologically compatible anti-microbial formulation that can also provide the cleansing effects of a surfactant-based formulation.

In an embodiment, an eyelid cleanser composition contains: (a) a hypohalous acid; (b) one or more surfactants having a HLB value of 5 to 18; and (c) an aqueous vehicle, the aqueous vehicle comprising: (i) one or more tonicity adjusters; (ii) one or more osmolality adjusters configured to adjust an osmolality of the composition; and (iii) one or more pH adjusters for adjusting the pH of the composition at between about 4.5 to about 8.0. The composition can be dispensed in a foam, liquid, spray, mist, gel or lotion form. The composition can facilitate long term eyelid hygiene by removing excess oil, debris and desquamated skin and also provide relief for inflammation of the eyes.

In a preferred embodiment, the hypohalous acid is hypochlorous acid. The composition can contain from 10 to 1000 ppm of hypochlorous acid. In certain embodiments, the composition contains from 50 to 300 ppm of hypochlorous acid.

Preferably, the composition has one or more surfactants having a HLB value from 10-18. When the composition includes a combination of surfactants, at least a first surfactant has a HLB value from 10 to 18 and a second surfactant has a HLB value from 5-10. The one or more surfactants are selected from the group consisting of nonionic and amphoteric surfactants. In certain embodiments, the one or more surfactants are selected from the group consisting of sorbitan, sorbitan monolaurate, polyoxyethylene or polyethylene glycol (PEG) modified molecules such as PEG-modified surfactants, PEG-modified phospholipids, PEG-modified sugars, amineoxides, block copolymers and mixtures thereof. A total concentration of the one or more surfactants in the composition is in the range of 0.01 to 20% w/w of the total composition. In certain embodiments, the total concentration of the one or more surfactants in the composition is in the range of 0.01-5% w/w.

The composition is physiologically compatible and isotonic/isoosmolar. The tonicity adjuster can be selected from the group consisting of sodium chloride, potassium chloride, calcium chloride, magnesium chloride, sodium lactate, potassium lactate, calcium lactate and mixtures thereof.

The osmolality adjusters are configured to adjust an osmolality of the composition from 100 mOsm/kg to 500 mOsm/kg. The osmolality adjusters can be selected from the group consisting of sugars, glycerin, propylene glycol and mixtures thereof.

In one or more embodiments, the composition contains a foam stabilizer. The foam stabilizer can be a polyethylene glycol diester of methyl glucose and a fatty acid.

In one or more embodiments, the composition includes 0.01-5% w/w of one or more ingredients selected from the group consisting of propylene glycol, glycerin, liquid polyols, nut oils and derivatives, floral extracts, fruit extracts, sodium alginate, hyaluronic acid, diglycerides, triglycerides, PEG-75 Lanolin, mineral oil, silicone oil and mixtures thereof.

In one or more embodiments, the composition includes 0.01-5% w/w of one or more ingredients selected from the group consisting of an antioxidant, an anti-irritant, a cooling agent, a viscosity modifier and mixtures thereof.

In another embodiment, a kit for maintaining eyelid hygiene consists essentially of an applicator and the eyelid cleanser composition disclosed herein. The applicator can include a hypoallergenic, non-woven, hydrophilic material.

In yet another embodiment, a kit for maintaining eyelid hygiene consists essentially of an applicator pre-moistened with an effective amount of the eyelid cleanser composition disclosed herein. The applicator can include one or more fabric pads, wherein each pad is individually packaged in a sealable package.

In another embodiment, a method for managing eyelid care involves the application of an effective amount of the eyelid cleanser composition disclosed herein to the eyelids and its surrounding areas. The composition can be either left on or rinsed off after application.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

As used herein, all weight percentages (wt. %) are based on the total wt. % of the skin care composition, unless otherwise specified. Additionally, all composition percentages are based on totals equal to 100 wt. %, unless otherwise specified.

The compositions and methods for their use can "comprise," "consist essentially of," or "consist of" any of the ingredients or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the ingredients of the present invention and do not exclude other ingredients or elements described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment, the terms are defined to be within 5%. The term "substantially" and its variations are defined as being largely but not necessarily wholly what is specified as understood by one of ordinary skill in the art, and in one non-limiting embodiment substantially refers to ranges within 0.01%-5%.

As used herein, the term "effective amount" of a composition refers to an amount sufficient to elicit the desired biological response. As will be appreciated by those of ordinary skill in this art, and effective amount of a substance may vary depending on such factors as the desired biological endpoint, the patient, etc. The terms effective amount and clinically effect may be used interchangeably herein. For example, a effective amount/clinically effective amount of the composition is the amount that can be used facilitate long term eyelid hygiene while also substantially reducing inflammation and promoting wound healing of the eyelids.

While the specification concludes with the claims particularly pointing and distinctly claiming the invention, it is believed that the present invention will be better understood from the following description.

The eyelid cleanser composition is an ophthalmic/ocular composition that can clean the eyelids and eyes and remove excessive oil, debris, and desquamated skin from the eyelids and surrounding areas while reducing inflammation and promoting wound healing. The composition contains a hypohalous acid, one or more surfactants having a hydrophile-lipophile balance (HLB) value ranging between 10 and 18, and an aqueous vehicle containing one or more components for adjusting the pH, tonicity, osmolality of the composition.

The "hal" of the hypohalous acid is a halogen selected from the group consisting of chloro, bromo, iodo and fluoro. Preferably, the halogen is chloro and the hypohalous acid is hypochlorous acid. The composition contains at least 10-1000 ppm of hypochlorous acid. In certain embodiments, the composition contains 50-300 ppm of hypochlorous acid.

One or more nonionic or amphoteric surfactants can be used in the formulation to achieve a desired foaming capacity and/or cleansing capability. The inclusion of a surfactant will enhance the ability of the composition to dissolve and remove oil, debris and desquamated skin. Preferable surfactants have a foaming ability and include nonionic or amphoteric surfactants having a HLB value between 10 and 18. If more than one surfactant is used, then at least one surfactant should has an HLB value between 10 and 18 and the other surfactant(s) should either have an HLB between 10 and 18 or an HLB value between 5 and 10. Suitable surfactants that may be used include, but are not limited to, sorbitan esters (such as, without limitation, Span 20 or sorbitan monolaurate, or the polyoxyethylene derivatives of sorbitan esters), polyethylene glycol (PEG) modified surfactants (such as, without limitation, polysorbate 80, Brij 52, PEG-75 Lanolin), modified phospholipids, modified sugars (such as, without limitation, alkyl polyglucosides, fatty acid glucamides), aminoxides, and/or block copolymers such as, Pluronics (Pluronic F120, Poloxamer 188). The total concentration of surfactants can be in the range of 0.01 to 20% w/w of the final formulation but, more preferably in the 0.01-5% range.

The aqueous vehicle can be deionized water or purified water USP. The composition is physiologically compatible and isotonic/isoosmolar. The aqueous vehicle includes one or more components for adjusting tonicity, osmolality and pH, as needed. Preferred tonicity adjusters include one or more salts, such as, chlorides of sodium, potassium, calcium and magnesium, and sodium/potassium/calcium lactate. Osmolality can be adjusted using sugars, glycerin, propylene glycol and similar ingredients. The osmolality of the composition can be adjusted from about 100 mOsm/kg to about 500 mOsm/kg. In certain embodiments, the osmolality of the composition is maintained at about 180 to about 400 mOsm/kg. The osmolality adjuster can include sugars, glycerin, propylene glycol and mixtures thereof and other similar ingredients.

Optimally, the pH of the composition is kept between 4.5 and 8.5, or preferably between a pH range between 5.0 and 7.0. The pH can be adjusted without the use of traditional pH adjusters which can be irritating to the eye. For instance, the pH of the composition may be adjusted by adding buffering components such as phosphate salts, citrate salts, tris salts and the corresponding acids/bases in defined ratios to target the desired pH when the aqueous vehicle is prepared or by adding incremental amounts of an acid or a base with stirring until the desired pH is reached once all ingredients have been dissolved/dispersed.

The inclusion of hypochlorous acid provides the composition with an antimicrobial activity. The antimicrobial activity will vary depending on the concentration of hypochlorous acid, the presence of one or more surfactants, and the pH of the composition. Maintaining the pH of the composition will also optimize the stability of the hypochlorous acid, its antimicrobial activity, and reduce any negative reactions with the skin or eyelid if applied to the eyelid or skin and not washed off.

Although optional, a foam stabilizer can be added to the composition, and may include, without limitation, a polyethylene glycol diester of methyl glucose and a fatty acid. The fatty acid can be selected from a group consisting of oleic acid, stearic acid, lauric acid, caprylic acid, and capric acid. Preferably, the one or more foam stabilizers includes PEG-120 methyl glucose dioleate.

The composition can also include additional components in amounts up to a 5% w/w of the composition. These components include one or more moisturizers, emollients, humectants, or lubricants are also commonly added to the composition and are generally referred to herein as moisturizers. Suitable moisturizers are propylene glycol, glycerin, polyethylene glycol (e.g. PEG 300, 400, 600) or generally, liquid polyols, nut oils and derivatives, floral extracts, such as, rose extracts, fruit extracts such as cucumber extract, sodium alginate, hyaluronic acid, medium chain diglycerides, medium chain triglycerides, PEG-75 lanolin, mineral oil, silicone oil and mixtures thereof.

The composition further includes up to 5% w/w of one or more optional components including such compounds as antioxidants (such as, without limitation, Vitamin E and its derivatives, green tea extract, Vitamin C and its derivatives), anti-irritating/soothing agents (such as, without limitation, allantoin, aloe vera, tea tree oil), cooling agents (such as, without limitation, sorbitol, xylitol, menthol, thymol), and viscosity modifiers (such as, without limitation, carboxymethyl cellulose, hydroxypropyl methylcellulose, Carbopol®). The viscosity of the composition is preferably greater than 10 cps. In certain embodiments, the viscosity can also be in the range of 1-10 cps.

In an embodiment, a method of manufacturing the composition is disclosed. The method involves mixing the ingredients disclosed herein into the aqueous vehicle in order of increasing concentration with constant mixing (low shear) until all water-miscible/water-soluble ingredients are homogenously dissolved/dispersed within the vehicle. In the embodiments that involve oil soluble ingredients, a separate oil phase may be prepared (at 30-70° C.) and then added to the aqueous phase with vigorous stirring at 30-70° C. (depending on stability of ingredients) until a homogenous dispersion is formed.

The eyelid cleanser composition is typically applied to the surface of the eyelid and surrounding areas in the form of a spray, mist, foam or gel. In certain embodiments, the composition may be applied for a duration/frequency prescribed by a physician. The composition may be either left on the surface of the eyelid or surrounding areas or it can be wiped off after use. Whenever, the composition is used as a wipe-off formula, a hypoallergenic non-woven, hydrophilic material is recommended for best results. The composition can be configured to be non-residue forming. The composition is not to be used on open wounds, scars, or visible signs of inflammation, eczema and allergic rash. The composition can be clear to translucent and be colorless to yellowish in appearance.

The eyelid cleanser composition can be contained and dispensed from a suitable receptacle/dispenser. In certain embodiments, the container is a pump dispenser configured to contain and deliver the eyelid cleanser composition as a pre-lathered foam. The eyelid cleanser composition can be selected from a group consisting of a solution, a foam, a gel, a spray, a lotion, a suspension, an emulsion, microemulsion, an ointment and combinations thereof. In certain embodiments, the composition may be biphasic, that is, having two distinct separate layers within a container that has to be shaken before application.

In certain embodiments, an eyelid cleaning kit can include one or more fabric pads or wipes impregnated/pre-moistened with a clinically effective amount of the eyelid cleanser composition. The term "pad" refers to a thick piece of fabric that is capable of holding or absorbing the eyelid cleanser composition. For example, the fabric can be a lint-free fabric, such as, rayon or another suitable material. In certain embodiments, the fabric pad may be a cotton pad. The pads may be single use disposable pads. The kit can also include between 1-100 pads. The pads may be sealed individually or wrapped within any suitable packaging.

In certain embodiments, the kit can include one or more single use dry pads. A desired amount of the eyelid cleanser composition may then be applied to a dry pad prior to using it to cleanse the eyelids. In another embodiment, the kit can include a swab or another suitable applicator/system that can be saturated with a desired amount of the eyelid cleanser composition.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. An eyelid cleanser composition comprising:
(a) a hypohalous acid;
(b) a combination of surfactants, wherein
  (i) a first surfactant has a HLB value from 10 to 18, and
  (ii) a second surfactant has a HLB value from 5-10; and
(c) an aqueous vehicle, the aqueous vehicle comprising:
  (i) one or more tonicity adjusters;
  (ii) one or more osmolality adjusters for adjusting an osmolality of the composition; and
  (iii) one or more pH modifiers for adjusting a pH of the composition to between about 4.5 to about 8.0,
wherein a total concentration of the combination of surfactants in the composition is in the range of 0.01 to 20% w/w.

2. The eyelid cleanser composition according to claim 1, wherein the hypohalous acid is hypochlorous acid, and wherein the composition contains from 10 to 1000 ppm of hypochlorous acid.

3. The eyelid cleanser composition according to claim 1, wherein the hypohalous acid is hypochlorous acid, and wherein the composition contains from 50 to 300 ppm of hypochlorous acid.

4. The eyelid cleanser composition according to claim 1, wherein the first and second surfactants are selected from the group consisting of nonionic and amphoteric surfactants.

5. The eyelid cleanser composition according to claim 4, wherein the first and second surfactants are selected from the group consisting of sorbitan, sorbitan monolaurate, polyoxyethylene or polyethylene glycol (PEG) modified molecules such as PEG-modified surfactants, PEG-modified phospholipids, PEG-modified sugars, amineoxides, block copolymers and mixtures thereof.

6. The eyelid cleanser composition according to claim 1, wherein a total concentration of the first and second surfactants in the composition are in the range of 0.01-5% w/w.

7. The eyelid cleanser composition according to claim 1, wherein the tonicity adjuster is selected from the group consisting of sodium chloride, potassium chloride, calcium chloride, magnesium chloride, sodium lactate, potassium lactate, calcium lactate and mixtures thereof.

8. The eyelid cleanser composition according to claim 1, wherein the one or more osmolality adjusters are configured to adjust an osmolality of the composition from about 100 mOsm/kg to about 500 mOsm/kg.

9. The eyelid cleanser composition according to claim 1, wherein the one or more osmolality adjusters is selected from the group consisting of sugars, glycerin, propylene glycol and mixtures thereof.

10. The eyelid cleanser composition according to claim 1, wherein the composition is in a foam, liquid, spray, mist, gel or lotion form.

11. The eyelid cleanser composition according to claim 1, further comprising a foam stabilizer.

12. The eyelid cleanser composition according to claim 11, wherein the foam stabilizer is a polyethylene glycol diester of methyl glucose and a fatty acid.

13. The eyelid cleanser composition according to claim 1, further comprising 0.01-5% w/w of one or more ingredients selected from the group consisting of propylene glycol, glycerin, liquid polyols, nut oils and derivatives, floral extracts, fruit extracts, sodium alginate, hyaluronic acid, diglycerides, triglycerides, PEG-75 Lanolin, mineral oil, silicone oil and mixtures thereof.

14. The eyelid cleanser composition according to claim 1, further comprising 0.01-5% w/w of one or more ingredients selected from the group consisting of an antioxidant, an anti-irritant, a cooling agent, a viscosity modifier and mixtures thereof.

15. A kit for maintaining eyelid hygiene, wherein the kit consists essentially of an applicator and the eyelid cleanser composition according to claim 1.

16. The kit according to claim 15, wherein the applicator comprises a hypoallergenic, non-woven, hydrophilic material.

17. A kit for maintaining eyelid hygiene, wherein the kit consists essentially of an applicator pre-moistened with a clinically effective amount of the eyelid cleanser composition according to claim 1.

18. The kit for maintaining eyelid hygiene according to claim 17, wherein the applicator comprises one or more fabric pads, wherein each pad is individually packaged in a sealable package.

19. A method for managing eyelid care, the method comprising the application of an effective amount of the eyelid cleanser composition according to claim 1 to the eyelids and its surrounding areas.

\* \* \* \* \*